United States Patent [19]
Coleman

[11] 3,931,827
[45] Jan. 13, 1976

[54] METHOD AND APPARATUS FOR STYLING SYNTHETIC WIGS

[76] Inventor: Edward H. Coleman, 2226 Fulton Ave., Cincinnati, Ohio 45206

[22] Filed: Sept. 17, 1973

[21] Appl. No.: 397,677

[52] U.S. Cl. .......................... 132/56; 132/7; 132/9
[51] Int. Cl.² ............................................. A41G 3/00
[58] Field of Search ............ 132/56, 7, 5, 9, 11, 40, 132/33 R; 312/116; 60/23; 8/130.1; 34/5

[56] References Cited
UNITED STATES PATENTS

| | | | |
|---|---|---|---|
| 841,175 | 1/1907 | Phinney | 132/11 |
| 1,871,553 | 8/1932 | Parker | 132/9 |
| 1,881,727 | 10/1932 | Page | 132/33 R |
| 2,110,463 | 3/1938 | Ferguson | 132/9 |
| 2,119,261 | 5/1938 | Andrews | 8/130.1 |
| 2,157,117 | 5/1939 | Miles, Jr. | 8/130.1 |
| 2,444,124 | 6/1948 | Wedler | 34/5 |
| 3,480,019 | 11/1969 | Popeil | 132/40 |
| 3,694,143 | 9/1972 | McCurry | 132/7 |
| 3,721,250 | 3/1973 | Walter | 132/11 |

Primary Examiner—G. E. McNeill
Attorney, Agent, or Firm—Wood, Herron & Evans

[57] ABSTRACT

This invention relates to a method and apparatus for styling synthetic wigs utilizing steam to soften the fibers and refrigeration to harden and set the fibers. A comb having steam emission openings located around the teeth of the comb applies steam to the wig as it is stroked through the fibers of the wig. A sealable container into which the wig may be placed and steam introduced allows the wig after it has been styled to be permeated with steam. A sealable container in which the wig may be placed, and the interior reduced in temperature, cools the wig to set the hair strands in the new style.

2 Claims, 1 Drawing Figure

U.S. Patent  Jan. 13, 1976  3,931,827
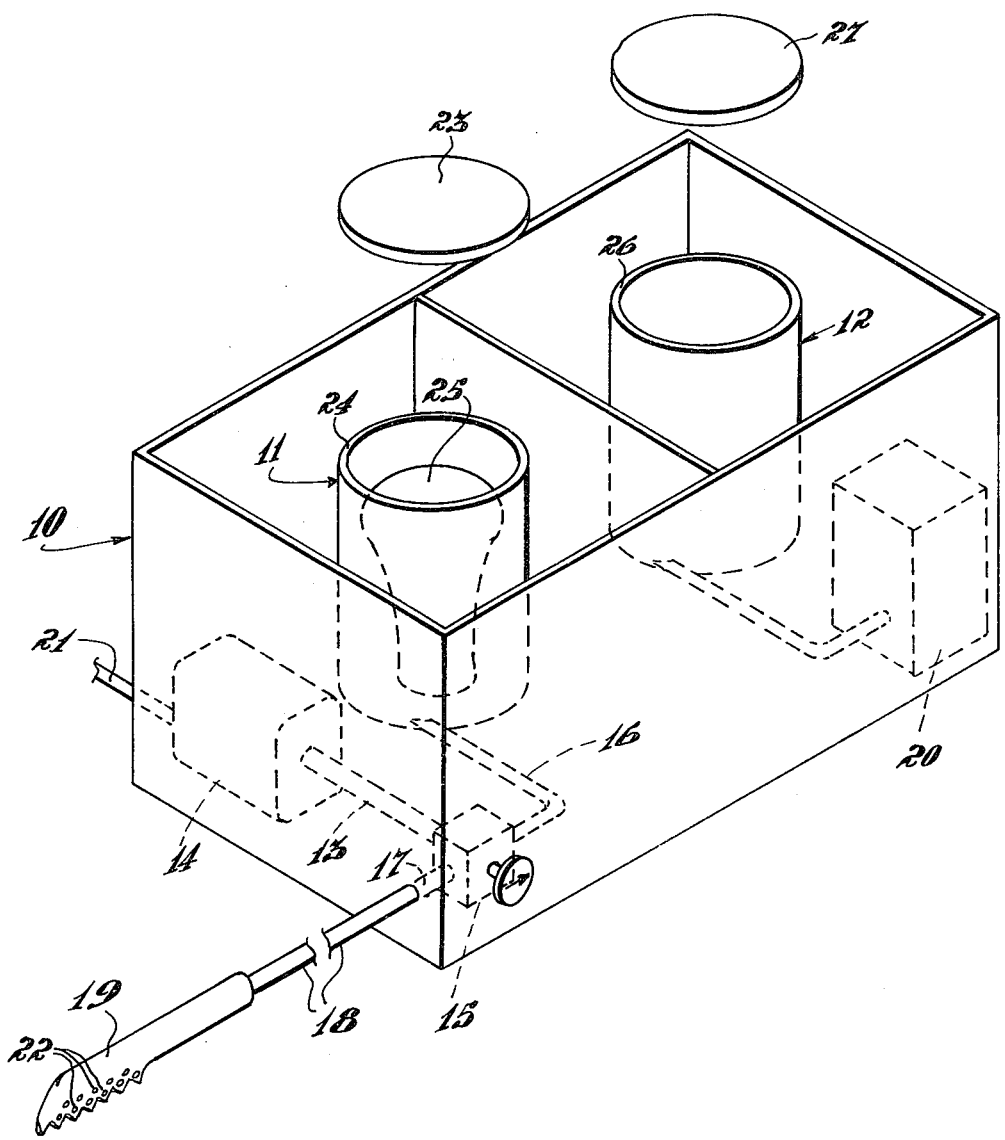

METHOD AND APPARATUS FOR STYLING SYNTHETIC WIGS

This invention relates to a method and apparatus for styling synthetic wigs.

In the past, there have been no practicable devices on the market with which synthetic wigs could be easily and economically styled in the convenience of either the home or the beauty salon. Generally, the style of a synthetic wig is set by the manufacturer so that common commercial treatments for styling and setting hair are ineffective. Over a period of time, however, a synthetic wig may become limp and lose its shape requiring restyling. Consequently, the owner's only recourse is to return the synthetic wig to the manufacturer or purchase a new wig.

The need for such a device is further manifested in the rapidly changing hair styles and in the growing number of fashion conscious individuals. As a result, the style of a synthetic wig quickly becomes unfashionable to wear, placing the owner in the unhappy situation of either appearing unfashionable or purchasing another wig. This problem has restrained the popular acceptance of synthetic wigs in favor of hair wigs which are easily restyled using common home and beauty salon treatments.

It has been an objective of the invention to provide a simple method and compact device with which a synthetic wig may be easily styled in the convenience of either the home or the beauty salon. More specifically it has been an objective of the invention to provide a method of styling synthetic wigs including the steps of putting up the strands into the desired style, steaming the styled wig to relax the strands and remove their "memory" of the prior set, and thereafter to refrigerate the strands to effect the setting of the new style.

It has been a further objective of the invention to provide simple apparatus for performing the method described above.

It has been another objective of the invention to provide a comb having steam emission openings adjacent the teeth of the comb, the comb being employed to soften and straighten the fibers of a previously styled wig prior to setting the new style.

The objectives of the invention will become more readily apparent from the following detailed description taken in conjunction with the accompanying drawing which is a diagrammatic perspective view illustrating the invention.

The apparatus of the invention includes an enclosure 10 which contains a steam chamber 11 and a refrigeration chamber 12. A steam outlet line 13 conducts the steam from a steam generator 14 into a bi-directional valve 15. A steam chamber inlet 16 conducts the steam into the steam chamber 11. A steam comb inlet 17 conducts the steam through a flexible tube 18 into a steam comb 19. A refrigeration unit 20 cools the inside of the refrigeration chamber 12.

DESCRIPTION OF THE PREFERRED EMBODIMENT

In the preferred embodiment, the enclosure 10 has an open top and is divided transversely into two compartments. Water supplied through the water inlet 21 flows into the steam generator 14 located in the first compartment. The steam generated therein at approximately 212° F. flows into the bidirectional valve 15. This valve may be selectively adjusted to conduct the steam into either the steam comb inlet 17 or the steam chamber inlet 16. The steam comb 19 is a sawtooth, hollow element having steam emission openings 22 located around the teeth of the comb. By adjusting the bi-directional valve 15 to conduct the steam into the steam comb inlet 17, steam flows through the flexible tube 18 into the steam comb 19 and escapes through the steam emission openings 22. By manually stroking the comb through the fibers of the synthetic wig, The fibers are thereby partially softened, allowing the strands to more easily be placed on rollers and the like during styling.

The steam chamber 11 is located in the first compartment of the enclosure. This is a hollow container 24 which may be cylincrical and of sufficient size to hold the entire wig. It is mounted so that the upper surface of the container is even with the upper surface of the enclosure. A removable cover 23 may be used to seal the container when steam is being applied inside the container. A wig block 25 is located inside the container 24 on which the wig may be placed after it has been styled on rollers and the like. Steam is conducted into the container 24 when the bi-directional valve 15 is adjusted to conduct the steam into the steam chamber inlet 16. Steam enters through the lowest portion of the container 24 thereby permitting the entire wig to be permeated with steam. The wig is allowed to be steamed for approximately five minutes after which it is removed from the container 24. This process allows the steam to soften the synthetic fibers and relax or dissipate any memory of a prior set.

The refrigeration chamber 12 is located in the second compartment of the enclosure. It includes a hollow and insulated container 26 of sufficient size to hold the entire synthetic wig when styled. It is mounted so that the upper surface of the container 26 is even with the upper surface of the enclosure, thereby permitting the remainder of the refrigeration unit 20 to be mounted in the unused portion of the second compartment. A removable cover 27 is used to seal the container during the cooling process. A wig block is located inside the container on which the wig is placed after it has been removed from the steam chamber 11. The synthetic wig is cooled at approximately 32° F. for five minutues. This process hardens the fibers of the wig and gives it a permanent set.

In the operation of the invention, the generator 14 is energized to create a supply of steam. The bidirectional valve 15 is operated to connect the steam generator to the steam comb 19. The comb is passed through the strands of a prevously styled wig to soften and straighten the fibers so that they are in a condition to be restyled. The fibers are then put up using rollers, hairpins, and the like as is well known in the art. The thus treated wig is placed into the container 24 and the valve 15 is changed to direct steam into the steam chamber. After a suitable time, for example five minutes, the wig is removed from the steam chamber and placed in the refrigeration container 26. The cover 27 is placed over the container and the chamber is cooled to approximately 32° F. for another suitable period of time, for example 5 minutes. Thereafter the wig is removed. When the wig returns to room temperature, the rollers, hairpins, and the like are removed and the wig is combed out to the new style.

Having described my invention, I claim:

1. A method of styling synthetic wigs having synthetic fibers, the method comprising the steps of:
    steaming and stroking said wig fibers and thereby disentangling the fibers, straightening and softening said fibers and relaxing fiber memory of any prior set,
    putting the wig fibers up into the desired style,
    subjecting the put up fibers to steam to further relax fiber memory of any prior set, and
    thereafter cooling said fibers by subjecting the fibers to a temperature of approximately 32°F. for approximately 5 minutes, while the fibers are put up, in order to set them in the put up style.

2. Apparatus for treating synthetic wigs by steaming and stroking the fibers to straighten and disentangle them, by heating the fibers, while they are put up into a desired style, to relax fiber memory of previous sets, and by cooling the fibers to set them into the desired style, said apparatus comprising:
    a steam generator,
    a hair stroking implement having steam emission openings to direct steam onto said fibers when the implement strokes the fibers,
    means connecting said steam generator to said openings,
    a steam chamber,
    means connecting said steam generator to said chamber so that steam can be introduced into said chamber to treat said fibers and to relax fiber memory of a prior fiber set,
    a cooling chamber and means to cool the chamber to approximately 32 F. sufficient to set the synthetic fibers in the new set in which they are put up, and
    said means connecting the steam generator respectively to the openings in the stroking implement and to the steam chamber including a bidirectional valve selectively adjustable to conduct steam either into the stroking implement and through said openings, or into the steam chamber.

* * * * *